(12) United States Patent
Neuschäfer

(10) Patent No.: US 6,821,115 B2
(45) Date of Patent: Nov. 23, 2004

(54) APPARATUS FOR PREPARING AT LEAST ONE TOOTH FOR RECEIVING A CROWN, BRIDGE AND THE LIKE

(76) Inventor: Gerd Neuschäfer, Badestube 4, D-36251 Bad Hersfeld (DE)

( * ) Notice: Subject to any disclaimer, the term of this patent is extended or adjusted under 35 U.S.C. 154(b) by 229 days.

(21) Appl. No.: 10/165,476

(22) Filed: Jun. 7, 2002

(65) Prior Publication Data

US 2003/0008262 A1 Jan. 9, 2003

Related U.S. Application Data

(63) Continuation of application No. PCT/EP00/12132, filed on Dec. 2, 2000.

(30) Foreign Application Priority Data

Dec. 9, 1999 (DE) .......................... 199 59 383

(51) Int. Cl.[7] ................................. A61C 1/14
(52) U.S. Cl. ..................... 433/25; 433/49; 433/50
(58) Field of Search ..................... 433/25, 34, 37, 433/41, 45, 49, 50, 51, 76

(56) References Cited

U.S. PATENT DOCUMENTS

| | | | | |
|---|---|---|---|---|
| 53,347 A | * | 3/1866 | Schaffer ...................... 433/45 |
| 307,579 A | * | 11/1884 | Palmiter ...................... 433/41 |
| 1,407,840 A | * | 2/1922 | Cruttenden .................. 433/76 |
| 3,254,413 A | * | 6/1966 | Goro ........................... 433/76 |
| 3,445,935 A | * | 5/1969 | Marshall ...................... 433/51 |
| 3,626,594 A | * | 12/1971 | Zinner et al. ................ 433/45 |
| 4,941,826 A | * | 7/1990 | Loran et al. ................. 433/51 |
| 5,222,892 A | * | 6/1993 | Perry ........................... 433/75 |
| 5,340,308 A | * | 8/1994 | Cukjati ....................... 433/41 |
| 6,468,078 B2 | * | 10/2002 | Guillaume et al. ........... 433/45 |

FOREIGN PATENT DOCUMENTS

| | | |
|---|---|---|
| DE | 44 43 929 C1 | 12/1994 |
| EP | 0 769 063 B1 | 12/1995 |

* cited by examiner

Primary Examiner—Cary E. O'Connor
(74) Attorney, Agent, or Firm—Thomas, Kayden, Horstemeyer & Risley

(57) ABSTRACT

An apparatus serves to prepare at least one tooth (1) for receiving a dental element such as a crown, bridge and the like using a mould model (21) at least including one model tooth (23). The apparatus includes at least one positioning body (5), at least one parallelizing body (24), a mould spoon (12) including threaded sockets (17) and removable segments (20), a preparation base bar (46) including sliding elements (53), a tub (72), a transmitting unit (35), a transport arm mechanism (57), at least one unit (66) including position stabilizing arms (67), a plurality of model transfer bodies (78), and a copying grinding unit (90).

29 Claims, 12 Drawing Sheets

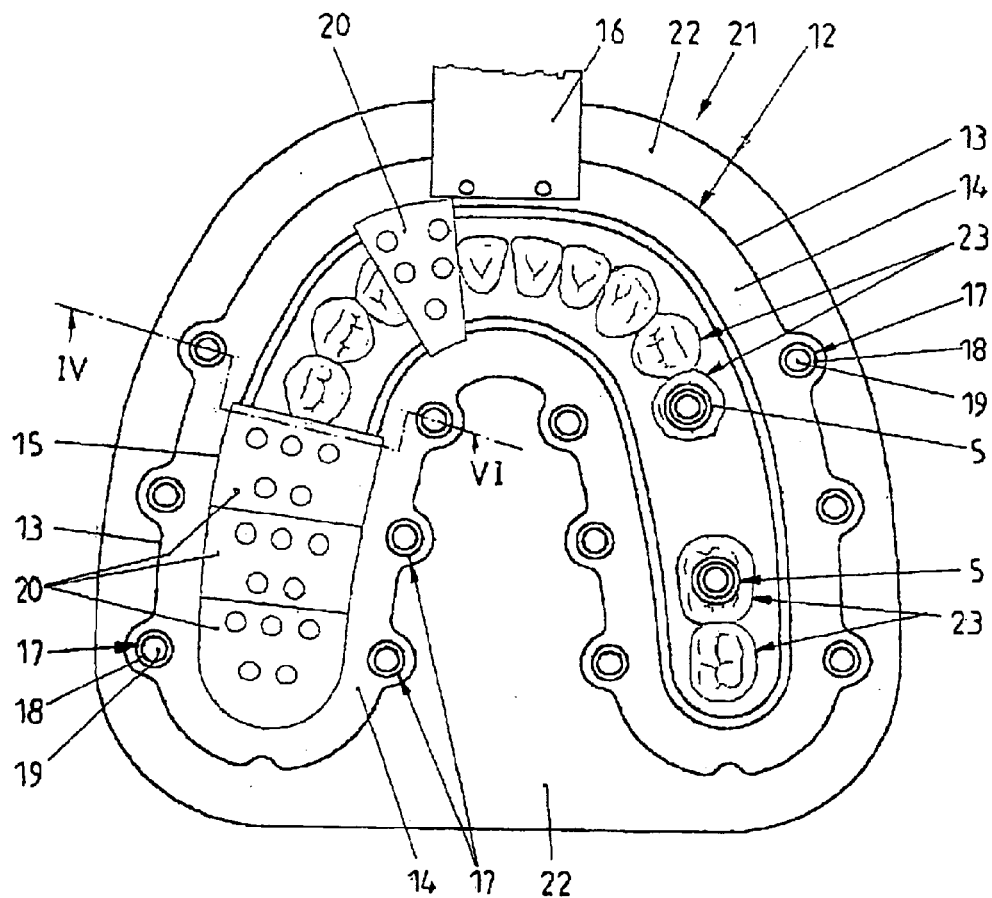
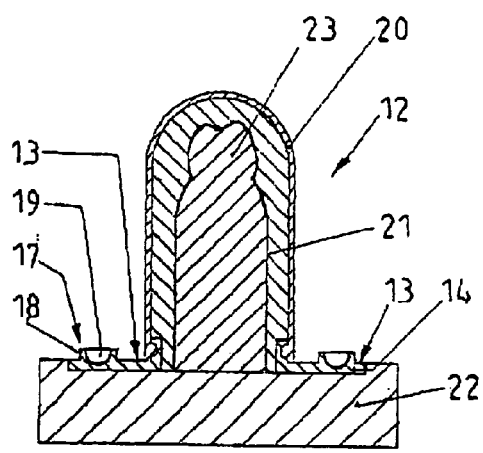
Fig. 3
Fig. 4

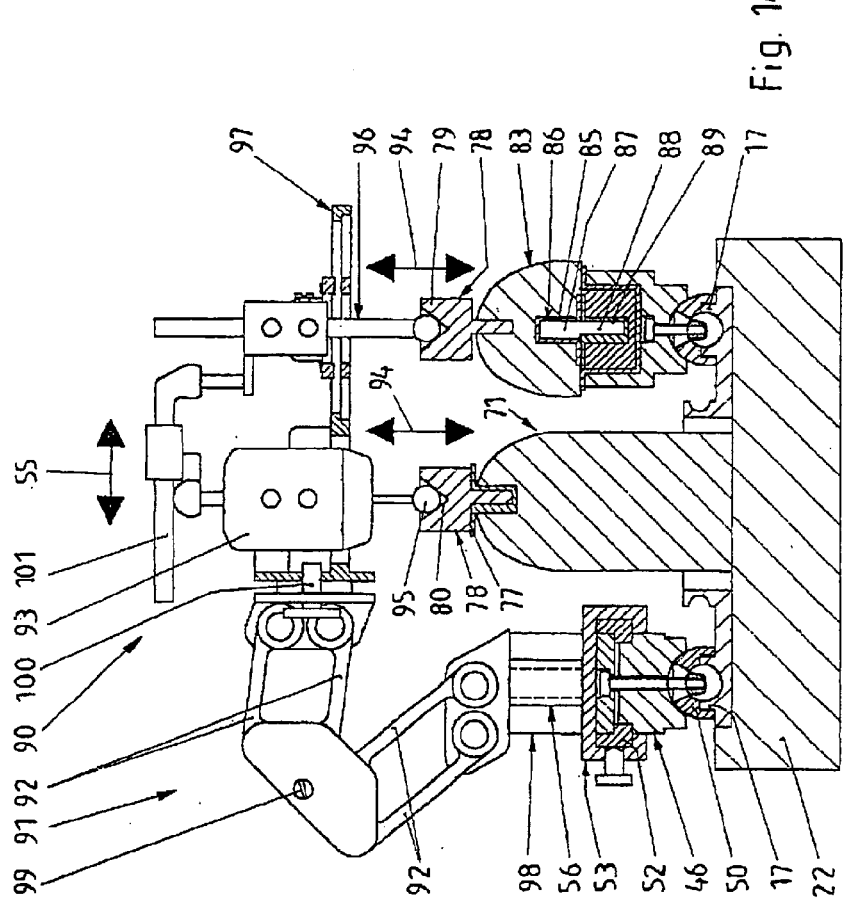

APPARATUS FOR PREPARING AT LEAST ONE TOOTH FOR RECEIVING A CROWN, BRIDGE AND THE LIKE

CROSS REFERENCE TO RELATED APPLICATIONS

This application is a continuation of International Application PCT/EP00/12132 with an international filing date of Dec. 2, 2000 and claiming the benefit of co-pending German Patent Application No. 199 59 383.3 entitled "Vorrichtung zur Präparation mindestens eines Zahnes zur Aufnahme einer Krone, Brücke o. dgl.", filed on Dec. 9, 1999.

FIELD OF THE INVENTION

The present invention generally relates to an apparatus for preparing at least one tooth for receiving a crown, bridge and the like. The tooth is prepared using a mould model at least including one model tooth. Crowns and bridges and other dental elements are used for the reconstruction of defect teeth and of gaps between teeth in human sets of teeth. A crown is used in combination with a single tooth, and a bridge is used to expend over a plurality of teeth.

BACKGROUND OF THE INVENTION

It is generally known in the art to reconstruct a tooth with a crown as follows:

The dentist first prepares the tooth to be reconstructed by grinding the tooth until a stub is received. Material of the tooth is removed to attain enough room for the crown. Grinding a tooth to form a stub requires substantial skills and concentration. Grinding is conducted by the dentist and in the mouth of the patient. Consequently, it is sometimes hard to correctly see the tooth, and reactions of the patient lower the quality of the preparation result. The required time for preparation is also influenced by the mouth anatomy, for example by adjacent teeth. After having prepared the tooth to form a tooth stub, a mould is produced in the mouth of the patient to attain a negative form corresponding to the tooth stub. The mould is then filled with plaster in a laboratory. Consequently, one attains a positive model, meaning a model tooth made of plaster. A technical crown is produced on this model tooth stub. The crown will be later placed upon the tooth stub, and it will be connected thereto using cement or different connection means. The exactness attainable with this known method is limited. Usually, extra work in the mouth of the patient is required. Especially, there may be problems in the region of the rim of the crown, meaning at the place where the crown closely contacts the natural tooth material.

A method of patient specific manufacture of and treatment with dental prosthetic work pieces is known from German Patent No. 44 43 921 C1 corresponding to European Patent No. 0 796 063 B1 and International Application PCT/EP95/04764 published under WO 96/17561. The method involves, first, taking an initial impression of the jaw to be treated including the checkbite in the mouth without earlier preparation steps. Then, a positive mould model of the jaw is produced followed by grinding of the mould model. The model in the resulting state is then stored by optical and/or mechanical scanning of the geometrical configuration of the mould model. Then, exclusively using the mould model, a crown or a bridge is produced in the known way. In the following, it is necessary to grind the natural tooth in the jaw of the patient using the stored data of the mould model, and to insert the crown or the bridge. In the known method, it is unclear in which way it is desired to attain a relation between the mould model and the tooth in the jaw of the patient. It is also unclear in which way the required intra oral milling unit is to be anchored and positioned, respectively, in the mouth of the patient.

SUMMARY OF THE INVENTION

The present invention relates to an apparatus for preparing at least one tooth for receiving a dental element such as a crown, bridge and the like using a mould model at least including one model tooth. The apparatus includes at least one positioning body, at least one parallelizing body, at least one mould spoon including threaded sockets and removable segments, at least one preparation base bar including sliding elements, at least one tub, at least one transmitting unit, at least one transport arm mechanism, at least one unit including position stabilizing arms, a plurality of model transfer bodies, and at least one copying grinding unit.

The present invention also relates to an apparatus for preparing at least one human tooth for receiving a dental element using a mould model at least including one model tooth. The apparatus includes at least one positioning body being designed to be inserted into an impression of a tooth to be prepared, a mould spoon including a spoon base and a plurality of segments and being designed to produce a mould model including at least one model tooth being designed to be connected to the positioning body, the segments being designed to be filled with a hardenable mass and being designed and arranged to be separately removable from the spoon base, the spoon base including a plurality of threaded sockets, at least one parallelizing body being designed to be placed upon the positioning body being connected to the model tooth to define a preparation axis, at least one preparation base bar being designed to be connected to the threaded sockets and including sliding elements, at least one transmitting unit being designed to be placed upon the parallelizing body and on the preparation base bar to transfer a reference plane perpendicular to the preparation axis to the preparation base bar, at least one tub being designed to be arranged on one of the threaded sockets to be filled with a hardenable mass, at least one transport arm mechanism being designed to be placed upon the transmitting unit and to align the plane of the preparation base bar to be parallel to the reference plane, at least one unit including position stabilizing arms and being designed to be placed upon the sliding elements, a plurality of model transfer bodies being designed to transmit a copying model of the prepared mould model to the mould spoon with positional accuracy, and at least one copying grinding unit being designed to grind the at least one tooth to be prepared scanning the copying model.

The present invention also relates to a mould spoon for producing a mould model of at least one human tooth to be prepared for receiving an dental element. The mould spoon includes a spoon base and a plurality of segments being connected to the spoon base, being filled with an impression mass, being designed to take an impression of the least one human tooth to be prepared and being designed and arranged to be separately removable from the spoon base.

The novel apparatus includes a plurality of elements and units. These elements and units are coordinated in a way to determine a preparation axis and a reference plane being located to be perpendicular with respect to the preparation axis. The elements and units of the novel apparatus are positioned and aligned in the reference plane and with respect to the reference plane, respectively. In this way, there is a family of parallel planes all being parallel with respect to the reference plane. The directions in these parallel planes are respectively maintained and transmitted to attain mutual orientation and to find, determine and find again the places at which process steps are to be conducted in an exact way. With the novel apparatus, it is possible to conduct most of the process steps outside of the mouth of the patient. Consequently, those process steps may be conducted at greater exactness and without negative influences by the patient.

The novel system includes a positioning body and an associated parallelizing body for each natural tooth. A common mould spoon or cast spoon with a mould base forms the base for this process. The preparation base bar and the sliding elements placed thereon are aligned and fixed to be parallel with respect to the reference plane. A tub serves to receive a copying model also being fixed in the tub with respect to the reference plane. A transmitting unit, a transport arm mechanism and at least one unit including position stabilizing arms for each tooth to be prepared serve to transmit the different parallel planes. Furthermore, the novel apparatus includes model transfer bodies to support the copying model at an exact position with respect to the preparation model at the mould spoon. Furthermore, the novel apparatus includes a copying grinding unit being designed and arranged to prepare the natural teeth, the copying model being used as a template. Exact positioning between the copying model and the natural teeth is important to this process. With the novel apparatus, it is possible to design, handle and insert crowns, bridges and other technical tooth portions at great exactness.

The novel apparatus has many advantages. Since the model teeth are shaped outside of the mouth of the patient without influences by the patient, the maximum attainable exactness of the crown and of the bridge, respectively, is substantially increased compared to the prior art. Misprepa- ration effects, as undercuts and divergences (in bridges) result in irrecoverable losses of tooth substance when pre- paring in situ. The novel method conducted with the novel apparatus limits the loss of tooth substance to the required minimum. Consequently, stability and biological resistance properties of the tooth stub are increased. The design of the model crown rim is more exact due to controlled prepara- tion. This also applies to the crown rim close to the natural tooth. The crown and the bridge, respectively, attains an aligned seat at the stub of the natural tooth. Consequently, caries occurring in the annular gap in the region of the rim is minimized. The usable times of the crown in the mouth are increased. Consequently, the cost for treatment of the patient is reduced. When using the novel apparatus, it is possible to conduct most of the process steps outside of the mouth of the patient resulting in increased precision and shortened nec- essary process times. Additionally, stress occurring during the treatment of the patient is also reduced both for the patient and for the dentist.

The positioning body preferably has an unround bottom plate and an upper part including an outer thread. The positioning body preferably in the region of its upper part has a comparatively smaller diameter. Preferably, the posi- tioning body is designed to be made of one piece, but it may also be made of a plurality of elements. The unround cross section of the bottom plate may be realized in different ways. It is especially simple to design the bottom plate to have a cylindrical shape, and to produce a flattened portion being arranged at one side. This flattened portion serves to insert, remove and put the positioning body back into a respective impression in the natural tooth in a way to prevent uninten- tional rotation. The upper part including an outer thread serves for the connection to a parallelizing body. The parallelizing body is designed and arranged to be rotatable with respect to the positioning body about ball surfaces. In this way, it is possible to define a preparation axis which is chosen to be located at the best place. With this preparation axis, one defines a reference plane which is of great impor- tance for all process steps, and which serves as reference for each process step.

The mould spoon or cast spoon is designed as a special mould spoon. As other mould spoons, it also includes a receiving space for receiving mould mass. However, the novel mould spoon has some special features. The novel mould spoon includes a spoon base having a protruding rim on which the thread sockets are arranged in a spaced apart manner. The segments forming a spoon housing are designed and arranged to be removable from the spoon base, and they may be placed back on the spoon base. The removable segments allow for processing a mould model exactly at the place where the natural teeth to be prepared require this. During most of the process steps, the mould spoon remains at its position at the mould model. It is not only a base for the impression, but also for all process steps to be taken at the mould model. Furthermore, the mould spoon serves to finally conduct process steps in the mouth of the patient, especially for copy grinding of the natural teeth. The mould spoon realizes the necessary relationship with respect to geometry.

The parallelizing body is used in combination with the positioning body. The parallelizing body includes a screwing piece including an inner thread, a connection piece, a ball and an axis screw, the screwing piece and the connection piece connecting each other by ball surfaces. The ball surfaces allow for an three-dimensional adjustment of the angle in space, and therefore for determining the preparation axis and the reference plane. At the same time, the paral- lelizing bodies in combination with a transmitting unit make it possible to transmit the preparation axis from one model tooth to another model tooth. This is necessary to operate in one common reference plane. This is especially important for inserting bridges and other technical elements which span a plurality of natural teeth and/or gaps between teeth.

The transmitting unit includes a base plate which forms a reference plane. The base plate includes a bush arranged perpendicular thereto and a sliding bush for determining and transmitting a preparation axis. The base plate with its plane forms the reference plane. The perpendicular position of the reference plane with respect to the preparation axis is realized by the bush being fixedly arranged on the base plate. The sliding bush is arranged to be movable at least in one direction in the plane of the base plate. The axes of the bush and of the sliding bush are located to be parallel with respect to each other. In this way, it is possible to transmit the preparation axis from a first model tooth to a second model tooth in parallel association.

The transmitting unit further serves to align a preparation base bar with a transport arm mechanism. The preparation base bar is aligned and determined to be parallel to the reference plane by an aligning frame. The association is realized by the mould spoon. With respect to meeting the correct angle association, the base plate includes a male protrusion having an unround circumferential surface. The male protrusion cooperates with a female protrusion having a respective unround circumferential surface and being located at the transport arm mechanism. Furthermore, there is such a connection between the transport arm mechanism and the preparation base bar.

The preparation base bar includes a base body, a fixing body, a fixing screw, a saddle head and a ball for determining the preparation axis, as well as an alignment frame for receiving the sliding members. The sliding members are designed and arranged to be movable on the alignment frame. They are moved in a plane parallel to the reference plane, and in a direction parallel to a direction connecting the preparation axes of the model teeth. The saddle head in combination with a ball and a fixing screw serves to determine the position of the preparation base bar in a plane parallel to the reference plane. The number of slide members corresponds to the number of natural teeth to be prepared and to possible gaps between teeth. When desired, the number of sliding members on the aligning frame may be varied.

The transport arm mechanism and/or the unit including the position stabilizing arms are designed to transmit parallel planes keeping the preparation axis. The transport arm mechanism and the unit including the position stabilizing arms have very similar designs, and a plurality of them may be included in the novel apparatus.

Furthermore, there is a model transfer body and a copying grinding unit. The model transfer body includes a pin foot element having an unround cross section and an unround head including a calibrating impression. The model transfer body serves to transmit a copying model of the preparation model to the mould spoon in an exact way and exactly at the right position. A tub with a hardenable mass is used, the tub being arranged on the spoon base. The tub is designed to be placed on a threaded socket of the mould spoon.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The following examples relate to the process of inserting a bridge, meaning the preparation of two teeth to be prepared. However, the components in the drawings are not necessarily to scale, emphasis instead being placed upon clearly illustrating the principles of the present invention. In the drawings, like reference numerals designate corresponding parts throughout the several views.

FIG. 3 is a top view of a mould model and a mould spoon.

FIG. 4 is a sectional view along line IV—IV in FIG. 3.

FIG. 14 is a similar sectional view during adjustment of a copying grinding unit.

FIG. 15 is a top view of a portion of the copying arm grinding unit.

DETAILED DESCRIPTION

Figure 1:
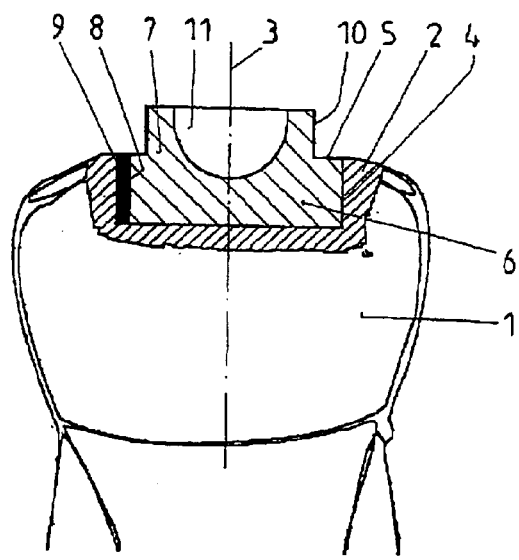
FIG. 1 is a partly sectional view of a natural tooth with an inserted positioning body.
Figure 2:
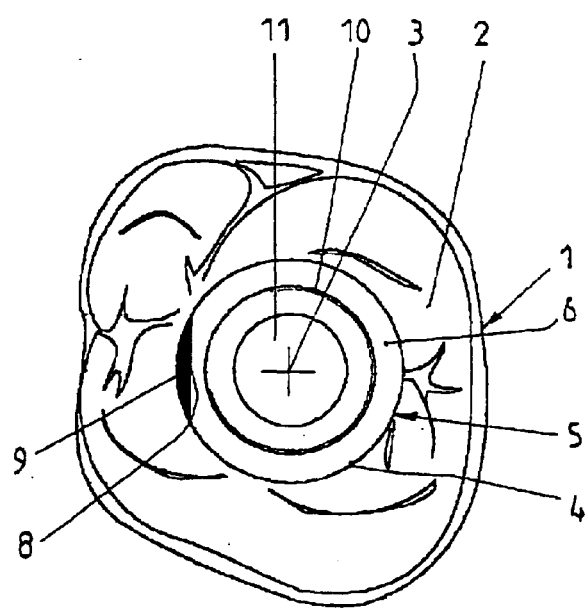
FIG. 2 is a top view of the natural tooth with the inserted positioning body.
Figure 5:
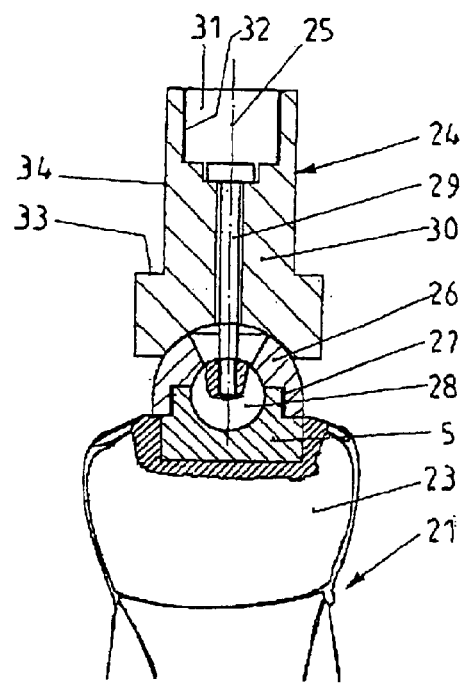
FIG. 5 is a view of a model tooth of the mould model including an inserted positioning body and a placed upon parallelizing body.

Referring now in greater detail to the drawings, FIG. 1 illustrates a natural tooth 1 which requires dental reconstruction. The tooth 1 includes a chewing surface 2 and a tooth axis 3. The tooth 1 is part of a set of teeth inside the mouth of a patient. Starting at the chewing surface 2, the dentist grinds a cylindrical impression 4 of limited depth in the direction of the tooth axis 3. A positioning body 5 includes a bottom plate 6 and an upper part 7. The diameter of the impression 4 is coordinated with the diameter of the bottom plate 6 of the positioning body 5. The positioning unit 5 with its bottom plate 6 is inserted into the impression 4 of the natural tooth 1. The bottom plate 6 of the positioning body 5 includes a flattened portion 8. Consequently, it has an unround design. The portion 8 with the impression 4 forms a hollow space 9 when the positioning body 5 is inserted. The hollow space 9 after having inserted the positioning body 5 is filled with a plastic, ductile material—for example plastic—which will later harden. The plastic material has properties such that it gets fixedly connected with the natural tooth 1, but not with the bottom plate 6 of the positioning body 5. Consequently, the positioning body 5 may be removed from the impression 4, the inserted plastic material remaining in the impression 4 of the tooth 1. In this way, the positioning unit 5 may be inserted into the impression 4 of the natural tooth 1 at an exact position and an exact angle, respectively, at any time.

The upper part 7 of the positioning body 5 has a cylindrical shape, and it includes an outer thread 10. The positioning body 5 in the region of the upper part 7 includes a recess 11 connected to its free surface. The recess 11 approximately has a hemispherical shape.

Another tooth 1 to be prepared is also treated in the above described way. There is a second positioning body 5 having the same design to be used for the second tooth 1. However, the positioning bodies 5 may have differently design portions 8 to prevent unintentional use of the wrong positioning body 5 at the wrong place.

The positioning bodies 5 are inserted into the impression 4 located in the natural tooth 1 located in the mouth of the patient at an exact position and at an exact angle, respectively, in a reproducible way. In the following, a mould is taken over the jaw in the mouth of the patient including the teeth 1. Moulding is realized by conventional impression masses, but with a special mould spoon 12 (FIG. 4). The mould spoon is somewhat similar to known mould spoons, and it fulfills a respective function. Different from known mould spoons, the mould spoon 12 includes a spoon base 13 being formed by a protruding rim being located at a spoon housing 15. A handle 16 is connected to the protruding rim 14 of the spoon housing 15. Furthermore, the spoon base 13 at different places includes threaded base elements to be connected to other components which will be described hereinbelow. Each threaded base element 17 includes an outer thread 18 and a recess 19 having an approximately hemispherical shape. The circumferential outer rim 14 of the spoon base element 13 has an irregular shape due to recess portions and protruding portions. The handle 16 is designed to be removable from the spoon base element 13. The spoon housing 15 of the mould spoon 12 is substantially formed by a plurality of separate segments 20. The entire spoon base element 13 may be closed with these segments 20. The single segments 20 are detachably connected to the spoon base element 13, and they may be separately removed and placed back on the spoon base 13 (FIG. 3). When the mould is taken, the positioning bodies 5 being inserted into the natural teeth 1 are embedded in the mould mass of the mould spoon 12 such that they are removed from the mouth of the patient together with the mould spoon 12 after the mould mass has hardened.

In this way, one attains a hollow space in the mould mass of the mould spoon 12. The hollow space may be filled with a respective material, for example plaster, in a known way. The hollow space in the mould mass of the mould spoon 12 is a negative mould form of the jaw. A positive mould model 21 (FIG. 3) having exactly the shape of the teeth and of the jaw inside the mouth of the patient results from filling the negative mould with plaster, for example. This positive mould model 21 includes model teeth 23 and also the positioning bodies 5 located in the model teeth 23 corresponding to the teeth 1. The positioning bodies 5 are located at exactly the same position in which they have been previously introduced into the impressions 4 of the natural teeth 1. Then, the mould model 21 still being located in the mould spoon 12 is connected to a base element 22, and it is fixedly connected to the base element 22. The base element 22 also contacts the outer rim 14 of the spoon base element 13. The mould spoon 12 is designed to be removable from the mould model 21 and to be placed upon it, respectively, the spoon base element 13 contacting recesses being located in the base 22.

After having completed the mould model 21 with the base 22, the segments 20 in the preparation region are removed from the spoon base 13 of the mould spoon 12. The mould mass is removed from the mould model 21 in this region. The mould spoon 12 is located on the base 22 of the mould model 21. Parallelizing bodies 24 are placed upon the positioning bodies 5 located in the model teeth 23 of the mould model 21. The parallelizing bodies 24 serve to determine a preparation axis 25. Each parallelizing body 24 includes a screw piece 26 including an inner thread 27, a ball 28, a screw 29 and an element 30 in its recess 31 including an inner thread 32. The two parallelizing bodies 24 with the respective inner thread 27 of the screw piece 26 are screwed upon the respective outer thread 10 of the upper part 7 of the positioning body 5 in a fixed way. The screws 29 are not yet tightened, but they instead remain lose such that the piece 30 may be really moved about the piece 26. Then, an optimum preparation axis 25 with respect to one of the model teeth 23 is determined, and the respective piece 30 is aligned in this direction, and it is fixed by tightening the respective screw 29. The preparation axis 25 fixed in this way corresponds to the insertion direction of the bridge and of the prosthetic work piece, respectively. One connection piece 30 attains a certain determined position with respect to the screwing piece 26, with respect to the positioning body 5 and finally with respect to the tooth crown of the respective model tooth 23. Each connection piece 30 at its outer side includes a step 33 and a cylindrical surface 34.

Figure 6:
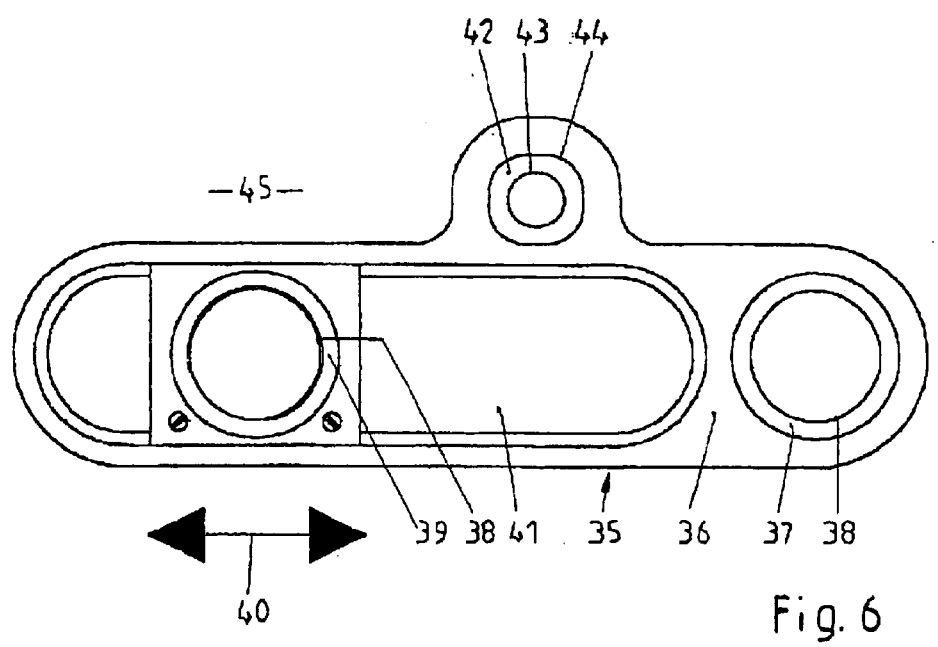
FIG. 6 is a top view of a transmitting apparatus.

There is a transmitting unit 35 (FIG. 6) serving to align the not yet fixed preparation axis 25 of the second parallelizing body 24 in a parallel position with respect to the already fixed preparation axis 25 of the first parallelizing body 24. The transmitting unit 35 includes a base plate 36 and a bush 37 being fixedly located on the base plate 36 approximately rectangular. The inner diameter 38 of the bush 37 is coordinated with the outer diameter of the cylindrical surface 34 of the connection piece 30. A sliding bush 39 having the same inner diameter 38 is located on the base plate 36 of the transmitting unit 35. The sliding bush 39 with its axis is also located with respect to the base plate 36 in a rectangular way, but it is supported within a recess 41 of the base plate 36 to be movable with respect to the base plate 36 in the direction of a double arrow 40. A male protrusion 42 including an inner thread 43 and an unround circumferential surface 44 is located at the side of the base plate 36 of the transmitting unit 35. The protrusion 42 with its axis is located to be perpendicular with respect to the base plate 36 such that the axes of the bush 37, the sliding bush 29 and the protrusion 42 are located to be parallel with respect to one another. The base plate 36 of the transmitting unit 35 forms a reference plane 45 being identical with the plane of illustration of FIG. 6.

The bush 37 of the transmitting unit 35 with the base plate 36 is pushed upon the connection piece 30 fixed by the screw 29. At the same time, the sliding bush 39 at the transmitting unit 35 is placed upon the unfixed connection piece 30 located at the other model tooth 23. During the sliding motion of the sliding bush 39, the connection piece 30 of the second parallelizing body 24 is aligned to be parallel to the axis of the first parallelizing body 24. The axes of the bush 37 and of the sliding bush 39 are arranged to be parallel, and they correspond to the preparation axis 25 and consequently to the insertion movement of the bridge.

Figure 7:
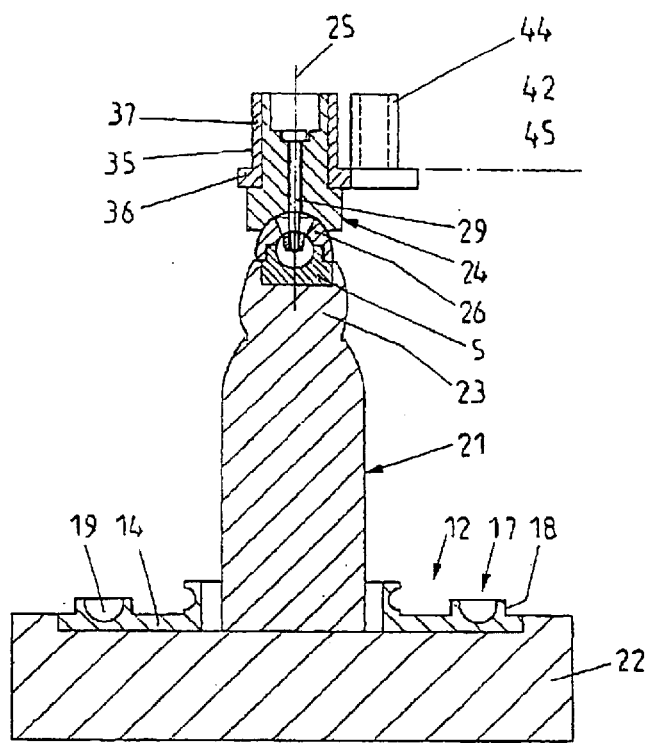
FIG. 7 is a sectional view similar to FIG. 4 showing a positioning body being inserted into the model tooth, a placed upon parallelizing body and a placed upon transmitting apparatus.
Figure 8:
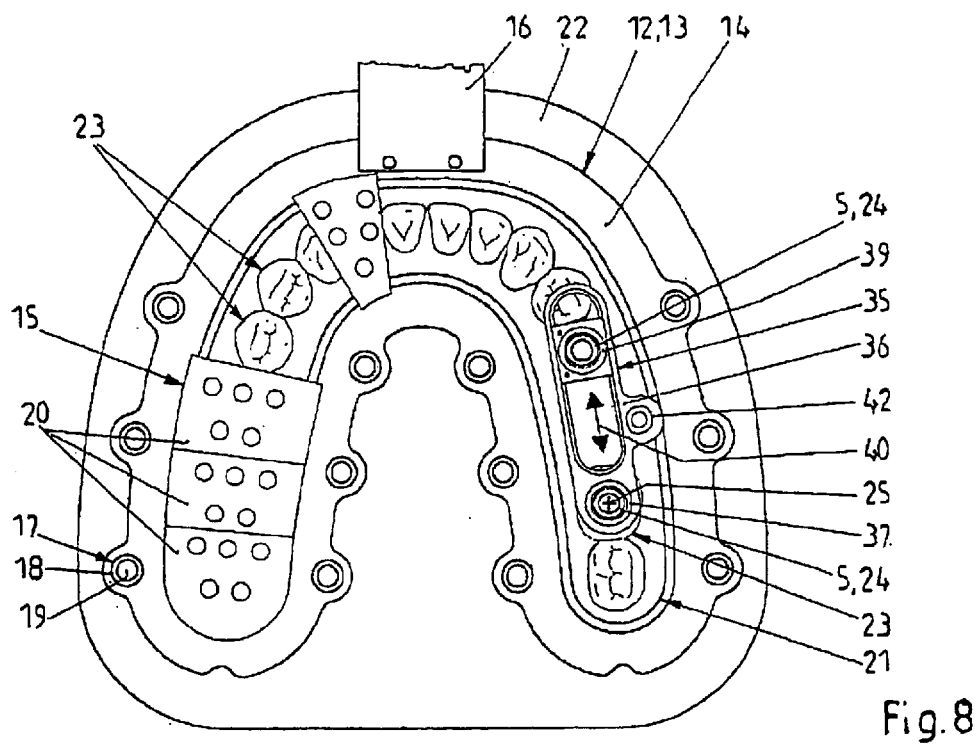
FIG. 8 is a top view of the mould model including a mould spoon and a transmitting apparatus.

Now, the screw 29 of the not yet fixed connection piece 30 is tightened (FIGS. 7 and 8), and the second parallelizing body 24 is thereby also determined with respect to its screwing piece 26. The two axes of the bush 37 and of the sliding bush 39 are located to be perpendicular with respect to the base plate 36 of the transmitting unit 35. The base plate 36 of the transmitting unit 35 connected to the two parallelizing bodies 24 forms the reference plane 45 for all following procedures, especially for parallel movements and transmitting movements.

Figure 11:
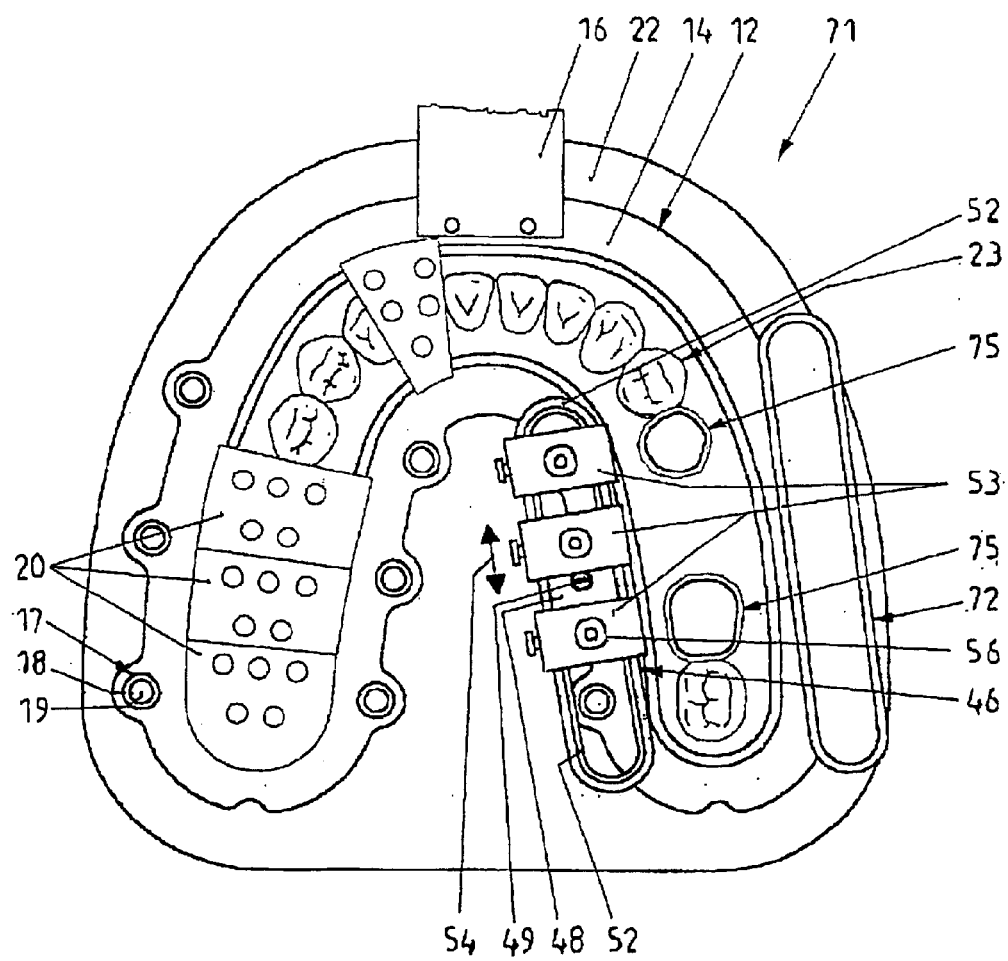
FIG. 11 is a top view of the preparation model including a placed upon preparation base bar and a tub.

There is a preparation base bar 46 (FIG. 9) including a base body 47 associated with a fixing body 48. The head of a fixing screw 49 is supported in the fixing body 48. The fixing screw 49 protrudes through the base body 47 and a saddle head 50, and it engages a thread being located in a ball 51. The saddle head 50 with an inner thread is fixedly screwed on the outer thread 18 of the threaded base 17 such that the ball 51 is fixedly arranged in the recess 19 of the threaded base 17. The preparation base bar 46 includes an aligning frame 52 being supported between the base body 47 and the fixing body 48 in a way that it may be moved and clamped. Sliding elements 53 are pushed upon the aligning frame 52 of the preparation base bar 46 (FIG. 11), the sliding elements 53 being freely movable with respect to the aligning frame 52 in a direction perpendicular to the plane of illustration of FIG. 9 and consequently in the direction of the double arrow 54 (FIG. 11). Each of the sliding elements 53 includes a stud screw for a fixed connection. Each sliding element 53 further includes a male protrusion 56 similar to a protrusion 42 located at the transmitting unit 35 also including an inner thread 43 and an unround circumferential surface 44.

Figure 9:
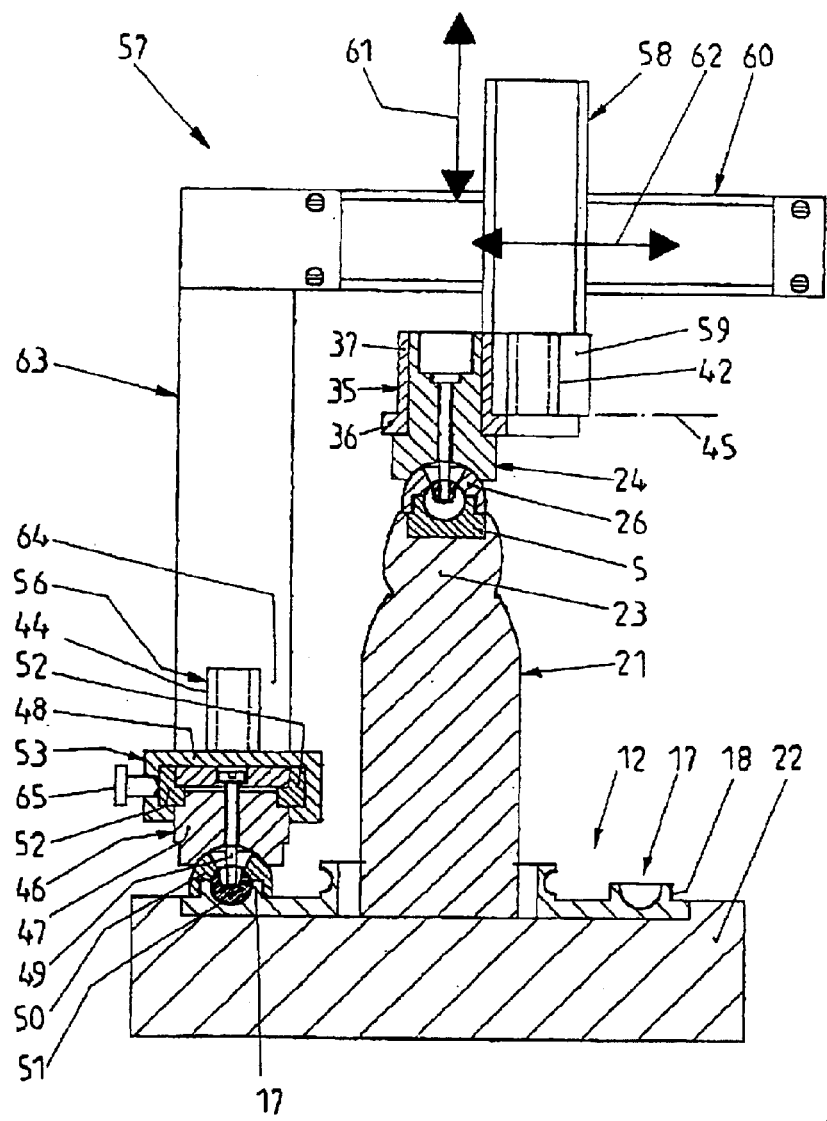
FIG. 9 is a sectional view similar to FIG. 4 or 7 and showing a preparation base bar and a transport arm mechanical unit.

A transport arm mechanical unit 57 is placed upon the transmitting unit 35 and perpendicular to the reference plane 45 (FIG. 9). The transport arm mechanical unit 57 serves to align the plane of the aligning frame 52 to be parallel to the reference plane 45. The transport arm mechanical unit 57 includes a column 58 the lower end 59 is designed to be fixedly pushed upon the protrusion 42 of the transmitting unit 35. The column 58 may be adjusted and fixed at an extension element 60 of the transport arm mechanical unit 57 in the directions of the two double arrows 61 and 62. The transport arm mechanical unit 57 includes another extension element 63 being permanently connected to the extension element 60 at a right angle. The lower end 64 of the extension element 63 may be pushed upon the male protrusion 56 not to be not rotatable.

The surface of the aligning frame 52 is aligned to be parallel with respect to the reference plane 45 by placing the lower end 59 of the column 58 onto the protrusion 42 of the transmitting unit 35 (FIG. 9) and by aligning the extension elements 60 and 63 according to the double arrows 61 and 62 on one of the sliding elements 53 in combination with placing the lower end 64 of the extension element 63 upon the male protrusion 56 and moving the sliding element 53 in the direction of the double arrow 54. As long as the fixing screw 49 is not tightened, the preparation base bar 46 is freely movable in a longitudinal direction and inside the frame of the recess 19 of the saddle head 50. The fixing screw 49 is then tightened, and the aligning frame 52 is thereby fixed in alignment to the threaded base 17. In the following, the transport arm mechanical unit 57 and the transmitting unit 35 are removed from the mould model 21. This process is to be seen from a comparison of FIGS. 9 and 10.

Additional sliding elements 53 are pushed upon the preparation base bar 46 (FIGS. 10 and 11) depending on the number of teeth 1 to be prepared and consequently on the number of model teeth 23 and the later required copying model transfer body. The sliding elements 53 may be locally fixed by stud screws 65. Each sliding element 53 includes a male protrusion 56 protruding in an upward direction. The protrusion 56 has an unround surface to realize an unrotatable connection. The male element 56 of each sliding element 53 may include an inner thread.

Figure 10:
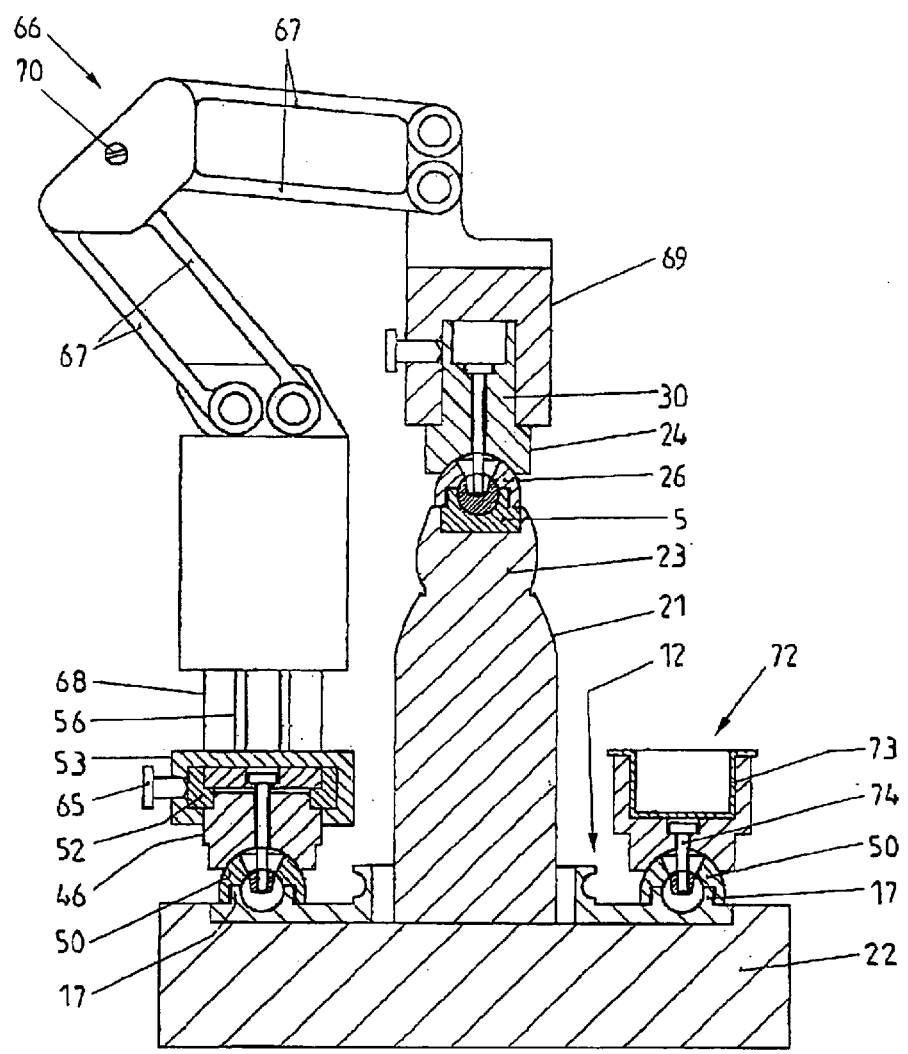
FIG. 10 is a sectional view similar to FIG. 9, but showing a placed upon unit including position stabilizing arms and a tub.

According to FIG. 10, units 66 including position stabilizing arms 67 are placed upon the male protrusions 56 of the freely movable sliding element 53 by a female mould 68. This is done successively for each model tooth 23 to be prepared. The position stabilizing arms 67 are suspended in the way of a parallelogram, and they are only movable in the plane of illustration of FIG. 10. Another female mould 69 is located at the other end of the position stabilizing arm 67, and it is connected to the connection piece 30 of the parallelizing body 24. A screw 70 serves to fix the position of the position stabilizing arm 67 with respect to each other. By tightening the screw 70, all degrees of freedom of the position stabilizing arm 67 are fixed. The respective sliding element 53 is fixed by tightening the stud screw 56 against the aligning frame 52 of the preparation base bar 46. It is loosened before the beginning of the intra oral preparation. The center sliding element 53 remains unused, and it is freely movable on the preparation base bar 46. Then, the first unit 66 is removed from the female protrusion 56 of the sliding element 53 and from the connection piece 30 of the parallelizing body 24 by the position stabilizing arms 67 in the fixed position. The same process repeats with respect to the second tooth 1 to be prepared and with respect to the second model tooth 23, respectively. The units 66 with the position stabilizing arms 67 are later required to insert the mould spoon 12 into the mouth of the patient. The positioning body 5 and the parallelizing body 24 are now removed from the model teeth 23 of the mould model 21 (FIG. 11). Later, they will be placed back in the natural teeth 1 to be ground.

The model teeth 23 of the mould model 21 are now formed in accordance with usual preparation rules. Consequently, there is a preparation model 71 resulting from the mould model 21. The prosthetic work piece (in this case the bridge) is produced on the preparation model 71. Later, meaning after the intra oral preparation, it is inserted into the mouth of the patient. A tub 72 is now (or before) fixed at the side of the preparation model 71 facing the preparation base bar 46 (FIG. 10). The tub 72 includes a removable inner tub 72 being located on a threaded base 17 of the mould spoon 12 being connected to the preparation model 71 (FIGS. 10 and 11). For this purpose, a saddle head 50 is fixedly screwed onto the outer thread 18 of a threaded base 17 at the respective position of the rim 14, and a fixing screw 74 engaging a ball 51 and protruding through the tub 72 is tightened. The mould spoon 12 with the preparation base bar 46 and the tub 72 is placed back on the preparation model 71. As a result, there is the view of the preparation model 71 according to FIG. 11 with the prepared model teeth 75.

A channel 76 (FIG. 12) for receiving a bush 77 is drilled at a place of the preparation model 71, for example between the two prepared model teeth 75, and perpendicular to the reference plane 45. This is done by aid of the transport mechanical unit 57 which is placed upon the center sliding element 53. The sliding element 53 is fixedly connected to the preparation base bar 46. The bush 77 includes an unround cross section, and it serves to support a model transfer body 78. The model transfer body 78 includes an unround head 79 having a front surface including a calibrate impression 80. The unround head 79 of the model transfer body 78 is supported in a female mould 81 at the transport arm mechanical unit 57 to be unrotatable. Furthermore, the model transfer body 78 includes a pin foot element 82 having an unround cross section coordinated with the unround cross section of the bush 77. The bush 77 together with the inserted model transfer body 78 together with the transport arm mechanical unit 57 is introduced into the channel 76, and it is fixedly connected therein, for example by glue (not illustrated in FIG. 12). The axes of the bush 77 and of the model transfer body 78 are aligned to be perpendicular with respect to the reference plane 45. The sliding element 53 carrying the transport arm mechanical unit 57 is now fixedly located on the preparation base bar 46 to keep its position. The transport arm mechanical unit 57 is then removed.

Figure 16:
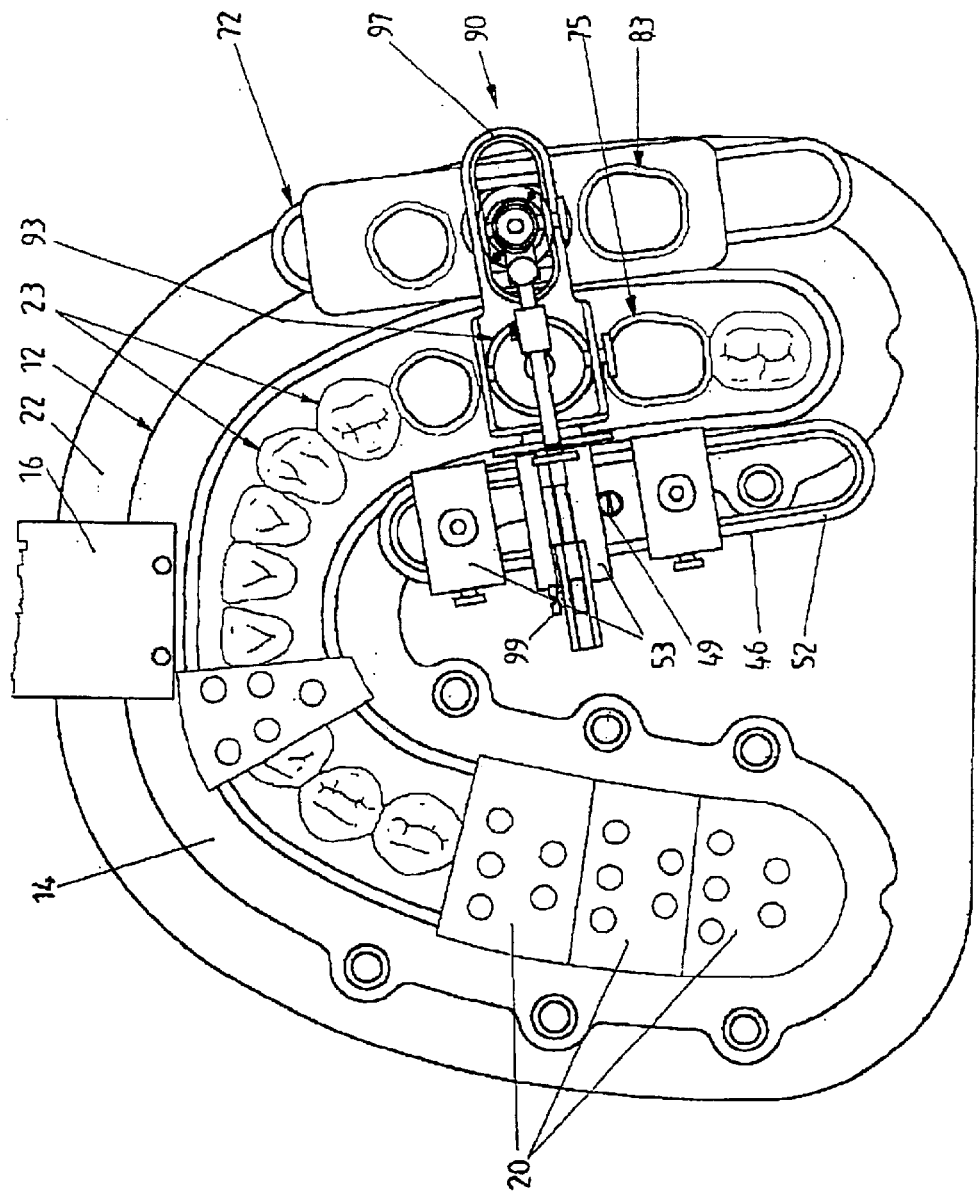
FIG. 16 is a top view of the mould model including the mould spoon, the copying grinding unit and the preparation model being inserted into the tub during adjustment.

Then, a mould is taken from the prepared portion of the preparation model 71 to produce a copy model 83. For this purpose, the mould spoon 12 is removed from the preparation model 71. The prepared portion of the preparation model 71 together with the model transfer body 78 being inserted into the bush 77 is then moulded with a conventional mould spoon being filled with mould mass. During removal of the hardened mould mass, the head 79 of the model transfer body 78 remains at its position in the mould mass, while the pin foot element 82 remains free. The (negative) hollow form of the mould mass is now filled with a material, especially with plaster. The (positive) copying model 83 results, the model transfer body 78 with its pin foot element 82 being embedded and anchored in the copying model 83. The head 79 of the model transfer body 78 has the right position with respect to the other elements of the copying model 83. The copying model 83 at its lower side facing away from the model transfer body 78 is ground at a right angle with respect to the model transfer body 78 and to be in one plane and not to consume too much space (FIG. 16). The copying model 83 later serves to transmit the shape of the prepared model teeth 23 to the natural teeth 1 by intra oral grinding.

A bore 84 is produced into the bottom side of the copying model 83 perpendicular with respect to the round surface, and consequently parallel with respect to the axis of the model transfer body 78. The bore 84 serves to support a bush 85 and a copying model fixing body 86. The copying model fixing body 86 includes a head 87 and a foot 88 both having unround cross sections. The head 87 is associated with the bush 85, and the foot 88 is associated with a bush 89. The bush 85 together with the head 87 is introduced into the bore 84, and it is permanently fixed. The bush 89 is placed upon the foot 88.

Figure 12:
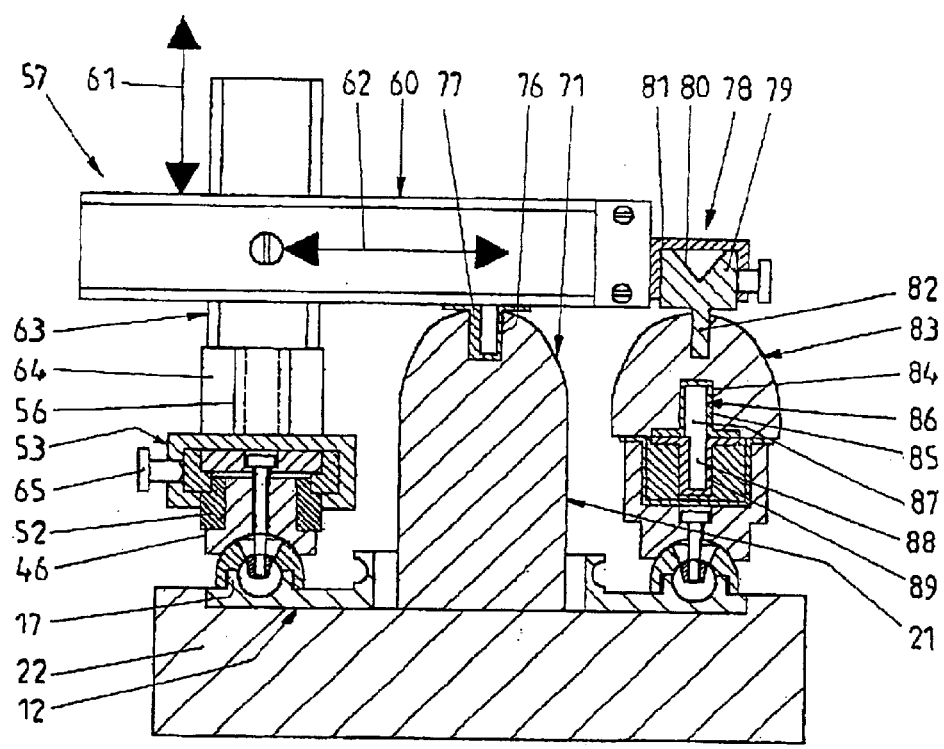
FIG. 12 is a sectional view similar to FIG. 4, 7 or 9 and showing a preparation base bar and a transport arm mechanical unit placed upon the mould spoon during positioning of a copy model in the tub.
Figure 13:
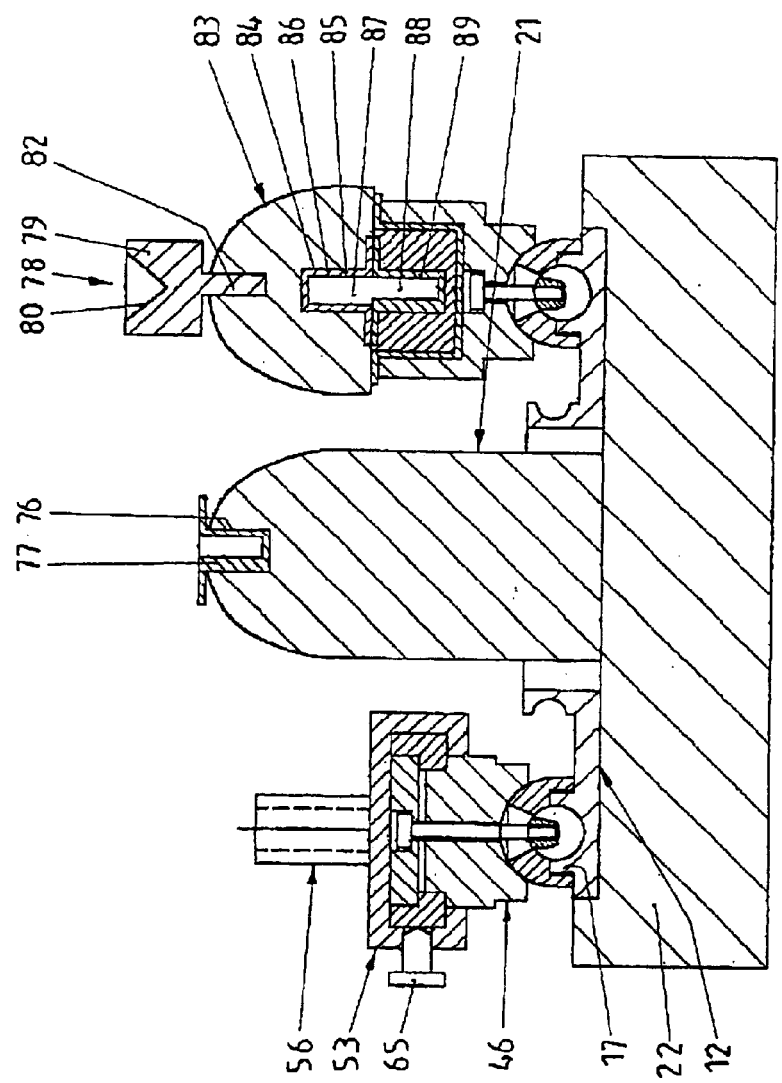
FIG. 13 is a sectional view according to FIG. 12 after removal of the transport arm mechanical unit.

The mould spoon 12 with its spoon 13 is placed back onto the preparation model 71 to receive a stable position. The model transfer body 78 in the copying model 83 is inserted exactly into the respective female mould 81 located at the extension element 60 of the transport arm mechanical unit 57, and it is fixed. The male protrusion 56 of the transport arm mechanical unit 57 is then pushed upon the male protrusion 56 of the fixed center sliding element 53, as this has already been done during positioning of the model transfer body 78. The copying model 83 together with the lowerable extension element 60 of the transport arm mechanical unit 57 is moved over the tub 72 fixed at the side facing the spoon base 13. The inner tub 73 is filled with a hardenable mass. The copying model 83 displays an parallel way is lowered until the extension element 60 contacts the empty bush 77 such that the copying model 83 displays in a parallel way and at the same height as the preparation model 71 is located in an aligned way above the tub 72. The bush 89 of the copying model fixing body 86 protrudes into the hardenable mass located inside the inner tub 73. The bush 89 is now fixed in the hardened mass in an irreversible way (FIG. 12). The copying model 83 may be removed from the bush 89 when desired, and it may also be placed back. The transport arm mechanical unit 57 is then removed. This position is illustrated in FIG. 13.

As it is to be seen from FIG. 14, a second model transfer body 78 having an identical design as the first model transfer body 78 is introduced into the bush 77. There is a copying grinding unit 90 which may be used in an intra oral way. The unit 90 includes a carrying unit 91 having a similar design as the unit 66. The carrying unit 91 includes carrying arms 92 being suspended in a way of a parallelogram. The copying grinding unit 90 includes a grinding head 93 with a rotational grinding body 95 which may be differently inserted in the direction of double arrow 94. Furthermore, it includes an element 96 of which the height may be changed and which may be moved in a lateral direction according to double arrow 55. The grinding head 93 and the element 96 are located on an extension element 97 at the carrying unit 91. The carrying arms 92 facing the preparation base bar 46 carry a female mould 98 which is placed on the male protrusion 56 of the fixed center sliding element 53. The plane of movement of the carrying arms 92 corresponds to the plane of illustration of FIG. 14. In this way, the extension element 97 and the elements fixed thereto move in a commonly aligned way in the plane of illustration. The movability of the carrying arms 92 may be fixed by a clamping screw 99. The extension element 97 with the grinding head 93 and the element 96 is arranged at the carrying unit 91 to be pivotable about a carrying axis 100. The movability may be locked by a pin located in a horizontal position. The grinding head 93 and the element 96 are suspended at the extension element 97 in a cardanic way, and they are commonly guided such that the axes of the grinding head 93 and of the element 96 always remain in a position parallel to one another. Both elements are movable in a synchronous way by a connecting mechanical unit 101. The movability may be locked, and it may be released.

Before the teeth 1 are prepared in an intra oral way, the copying grinding unit 90 has to be adjusted in an extra oral way (FIGS. 14 and 16). For this purpose, the mould spoon 12 is located on the base 22 of the preparation model 71. The copying model 83 is anchored in the tub 72. The empty bush 77 of the preparation model 71 is connected to a model transfer body 78. The intra oral copying grinding unit 90 with the female mould 98 is placed upon the protrusion 56 of the fixed center sliding element 53 facing the model transfer body 78, and it is fixed thereon in this way. The movability about the carrying axis 100 and synchronous movability of the grinding head 93 and of the element 96 are blocked. Now, the rotational grinding body 95 is lowered and fixed to the calibration impression 80 of the model transfer body 78 of the preparation model 71 (FIG. 4). The capability of movement of the carrying arms 92 is locked by tightening the clamping screw 99. The element 96 is then guided in a lateral direction over the calibrating impression 80 of the model transfer body 78 of the copying model 83, and it is adjusted in a way that the head of the element 96 is placed in the calibrating impression 80 of the model transfer body 78 of the copying model 83. The element 96 is fixed in this position. In this way, the copying grinding unit 90 is adjusted. Each position of the element 96 on the copying model 83 is associated with a respective position of the rotational grinding body 95 on the preparation model 71, and later at the natural teeth 1 in an intra oral way.

Blockage of the copying grinding unit 90 is released by releasing the clamping screw 99. At the same time, pivot ability of the grinding head 93 and of the element 96 are released. The intra oral copying grinding unit 90 is removed from the center sliding element 53 on the preparation base bar 46. It is returned after intra oral fixing of the mould spoon 12. The units 66 associated with the two model teeth 23 and including the position stabilizing arms 67 are now placed back on the associated fixed sliding elements 53, and they are connected thereon.

Consequently, all extra oral proceedings are finished. To get prepared for a intra oral preparation of the natural teeth 1, the positioning bodies 5 together with the parallelizing bodies 24 are introduced into the impressions 4 of the natural teeth 1 according to their code. The mould spoon 12 is removed from the base 22, and it is inserted into the mouth of the patient, the female mould 68 of the position stabilizing arms 67 of the units 66 being capable of being moved on the protrusions 56 of the sliding element 53, and the female moulds 69 on the connection pieces 30 of the parallelizing bodies 24. At the same time, the other natural teeth 1 and the jaw structure are embedded in the impressions of the mould mass in the region of the non-removed segments 20 of the mould spoon 12. Due to the alignment of the parallelizing bodies 24 and the impressions in the mould mass, the intra oral position of the mould spoon 12 and the one of the spoon base 13 are identical with their former position with respect to the preparation model 71 on the base 22.

Figure 17:
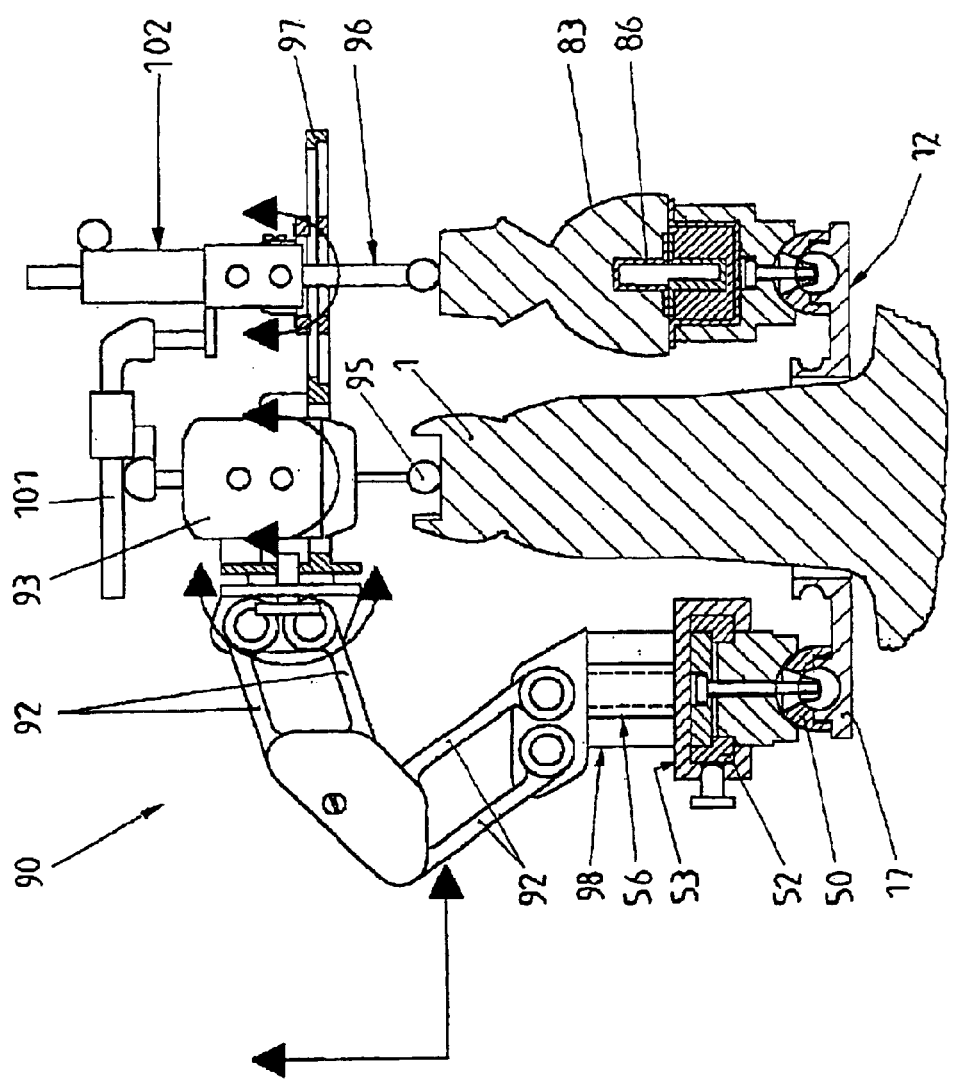
FIG. 17 is a partly sectional view showing the copying grinding unit and the mould spoon being inserted into the mouth of the patient.

The associated unit 66 with the position stabilizing arms 67 is now removed to prepare one of the teeth 1. The fixed position of the associated sliding element 53 is released, and the adjusted copying grinding unit 90 is placed on the sliding element 53 which is now movable. Due to the movability of the single elements of the copying grinding unit 90 and the movability of the sliding element 53, the rotational grinding body 95 may be moved and spaced in a three-dimensional way, as this is illustrated by the different arrows in FIG. 17.

The tooth 1 to be prepared is now ground by the copying grinding unit 90 under tracing of the copying model 83. The copying grinding unit 90 may be guided by hand, for example by a linkage of bars (not illustrated). A coupling pin 102 serves for the connection of the linkage of bars to the copying grinding unit 90. After preparation, the copying grinding unit 90 is removed from the sliding element 53, and instead the associated unit 66 with the position stabilizing arms 67 is placed on an fixed to the preparation base bar 46. The hollow space of the female mould 69 which is now free is filled with a fixing material, and it is lowered in the direction towards the prepared tooth 1 until the tooth 1 with its upper portion is embedded in the fixing material. The fixing material then hardens. The movability of the position stabilizing arms 67 is locked, again. In this way, the spoon base 13 of the mould spoon 12 regains its former stability.

In this way, all teeth 1 to be prepared are treated one after the other.

After having finished the preparation, the copying grinding unit 90 is removed from the mouth of the patient, and the ready to use prosthetic work piece (in this case the bridge) is inserted into the mouth of the patient.

Many variations and modifications may be made to the preferred embodiments of the invention without departing substantially from the spirit and principles of the invention. All such modifications and variations are intended to be included herein within the scope of the present invention, as defined by the following claims.

I claim:

1. An apparatus for preparing at least one tooth for receiving a dental element using a mould model at least including one model tooth, comprising:
    at least one positioning body being designed to be inserted into an impression of a tooth to be prepared;
    a mould spoon including a spoon base and a plurality of segments and being designed to produce a mould model including at least one model tooth being designed to be connected to said positioning body, said segments being designed to be filled with a hardenable mass and being designed and arranged to be separately removable from said spoon base, said spoon base including a plurality of threaded sockets;
    at least one parallelizing body being designed to be placed upon said positioning body being connected to said model tooth to define a preparation axis;
    at least one preparation base bar being designed to be connected to said threaded sockets and including sliding elements;
    at least one transmitting unit being designed to be placed upon said parallelizing body and on said preparation base bar to transfer a reference plane perpendicular to the preparation axis to said preparation base bar;
    at least one tub being designed to be arranged on one of said threaded sockets to be filled with a hardenable mass;
    at least one transport arm mechanism being designed to be placed upon said transmitting unit and to align the plane of said preparation base bar to be parallel to the reference plane;
    at least one unit including position stabilizing arms and being designed to be placed upon said sliding elements;
    a plurality of model transfer bodies being designed to transmit a copying model of the prepared mould model to said mould spoon with positional accuracy; and
    at least one copying grinding unit being designed to grind the at least one tooth to be prepared scanning the copying model.

2. The apparatus of claim 1, wherein said positioning body includes an unround bottom plate and an upper part having an outer thread, said positioning body in the region of its upper part having a reduced diameter.

3. The apparatus of claim 1, wherein said spoon base has a protruding rim on which said threaded sockets are arranged in a spaced apart manner, said segments being designed and arranged to form a spoon housing.

4. The apparatus of claim 1, wherein said parallelizing body includes a screw piece having an inner thread, a connection piece, a ball and a screw, said screw piece and said connection piece each including ball surfaces and being arranged to contact each other with said ball surfaces.

5. The apparatus of claim 1, wherein said transmitting unit includes a base plate being designed and arranged to form the reference plane, said base plate including a bush and a sliding bush being designed and arranged to determine and to transmit the preparation axis, said bush and said sliding bush each being arranged to be perpendicular with respect to the reference plane.

6. The apparatus of claim 5, wherein said base plate includes a male protrusion having an unround circumferential surface.

7. The apparatus of claim 1, wherein said preparation base bar includes a base body, a fixing body, a fixing screw, a saddle head and a ball being designed and arranged to determine the preparation axis, and an aligning frame being designed and arranged to support said sliding elements.

8. The apparatus of claim 1, wherein said transport arm mechanism is designed to transmit parallel planes maintaining the preparation axis.

9. The apparatus of claim 1, wherein said transport arm mechanism and said unit including said position stabilizing arms are designed to transmit parallel planes maintaining the preparation axis.

10. The apparatus of claim 1, wherein said unit including said position stabilizing arms is designed to transmit parallel planes maintaining the preparation axis.

11. The apparatus of claim 1, wherein said model transfer body includes a pin foot element having an unround cross section and an unround head including a calibrating impression.

12. The apparatus of claim 1, wherein said tub includes an inner tub, said tub with said inner tub being designed and arranged to be placed upon one of said threaded bases of said mould spoon.

13. The apparatus of claim 1, wherein said copying grinding unit includes a grinding head including a rotational grinding body being designed and arranged to be inserted into said grinding head at different positions, and an element being designed and arranged to change its vertical position and its lateral position.

14. An apparatus for preparing at least one tooth for receiving a dental element using a mould model at least including one model tooth, comprising:
- at least one positioning body;
- at least one parallelizing body;
- at least one mould spoon including threaded bases and removable segments;
- at least one preparation base bar including sliding elements;
- at least one tub;
- at least one transmitting unit;
- at least one transport arm mechanism;
- at least one unit including position stabilizing arms;
- a plurality of model transfer bodies; and
- at least one copying grinding unit.

15. The apparatus of claim 14, wherein said positioning body includes an unround bottom plate and an upper part having an outer thread, said positioning body in the region of its upper part having a reduced diameter.

16. The apparatus of claim 14, wherein said mould spoon includes a spoon base having a protruding rim on which said threaded sockets are arranged in a spaced apart manner, said segments being designed and arranged to form a spoon housing and to be removable from said spoon base and to be placed back on said spoon base.

17. The apparatus of claim 14, wherein said parallelizing body includes a screw piece having an inner thread, a connection piece, a ball and a screw, said screw piece and said connection piece each including ball surfaces and being arranged to contact each other with said ball surfaces.

18. The apparatus of claim 17, wherein said dental element is a crown.

19. The apparatus of claim 17, wherein said dental element is a bridge.

20. The apparatus of claim 14, wherein said transmitting unit includes a base plate being designed and arranged to form a reference plane, said base plate including a bush and a sliding bush being designed and arranged to determine and to transmit a preparation axis, said bush and said sliding bush being arranged to be perpendicular with respect to the reference plane.

21. The apparatus of claim 20, wherein said base plate includes a male protrusion having an unround circumferential surface.

22. The apparatus of claim 14, wherein said preparation base bar includes a base body, a fixing body, a fixing screw, a saddle head and a ball being designed and arranged to determine a preparation axis, and an aligning frame being designed and arranged to support said sliding elements.

23. The apparatus of claim 14, wherein said transport arm mechanism is designed to transmit parallel planes maintaining the preparation axis.

24. The apparatus of claim 14, wherein said transport arm mechanism and said at least one unit that includes position stabilizing arms are designed to transmit parallel planes maintaining the preparation axis.

25. The apparatus of claim 14, wherein said at least one unit that includes position stabilizing arms is designed to transmit parallel planes maintaining the preparation axis.

26. The apparatus of claim 14, wherein said model transfer body includes a pin foot element having an unround cross section and an unround head including a calibrating impression.

27. The apparatus of claim 14, wherein said tub includes an inner tub, said tub with said inner tub being designed and arranged to be placed upon one of said threaded bases of said mould spoon.

28. The apparatus of claim 14, wherein said copying grinding unit includes a grinding head including a rotational grinding body being designed and arranged to be inserted into said grinding head at different positions, and an element being designed and arranged to change its vertical position and its lateral position.

29. An apparatus for preparing at least one tooth for receiving a dental element using a mould model at least including one model tooth, comprising:
- at least one positioning body being designed to be inserted into an impression of a tooth to be prepared;
- a mould spoon including a spoon base and a plurality of segments and being designed to produce a mould model including at least one model tooth being designed to be connected to said positioning body,
- said segments being designed to be filled with a hardenable mass and being designed and arranged to be separately removable from said spoon base,
- said spoon base including a plurality of threaded sockets;
- at least one parallelizing body being designed to be placed upon said positioning body being connected to said model tooth to define a preparation axis;
- at least one preparation base bar being designed to be connected to said threaded sockets and including sliding elements.

* * * * *